United States Patent [19]
Bennett et al.

[11] Patent Number: 4,905,711
[45] Date of Patent: Mar. 6, 1990

[54] EYE RESTRAINING DEVICE

[75] Inventors: Peter S. Bennett, Newtown; G. Hilary Harrold, West Redding; Paul R. Yoder, Jr., Wilton, all of Conn.; Robert A. DelPero, Greenville, N.C.

[73] Assignee: Taunton Technologies, Inc., Monroe, Conn.

[21] Appl. No.: 165,535

[22] Filed: Mar. 8, 1988

[51] Int. Cl.$^4$ .............................................. A61B 19/00
[52] U.S. Cl. ........................................ 128/869; 606/4
[58] Field of Search ............... 128/303.1, 303 R, 305; 264/322, 328, 21, 56, 58, 59, 71, 74, 79–81

[56] References Cited
U.S. PATENT DOCUMENTS

| | | | |
|---|---|---|---|
| 4,019,727 | 4/1977 | Martin et al. | 269/328 |
| 4,173,980 | 11/1979 | Curtin | 128/303 |
| 4,378,108 | 3/1983 | Bailey, Jr. | 269/328 |
| 4,465,069 | 8/1984 | Barbier et al. | 128/303 |

OTHER PUBLICATIONS

"Advanced Techniques in Ophthalmic Microsurgery vol. II" by Louis Girard; the C. V. Mosby Company, pp. 156–159, 162–163.

Primary Examiner—Francis Jaworski
Assistant Examiner—David Shay
Attorney, Agent, or Firm—Kramer, Brufsky & Cifelli

[57] ABSTRACT

An eye restraining device includes a ring-shaped element which contacts the sclera of an eye so that the cornea projects above the ring-shaped element. A second embodiment includes a head restraint including a plurality of adjustable engaging components for accommodating different sized heads.

4 Claims, 5 Drawing Sheets

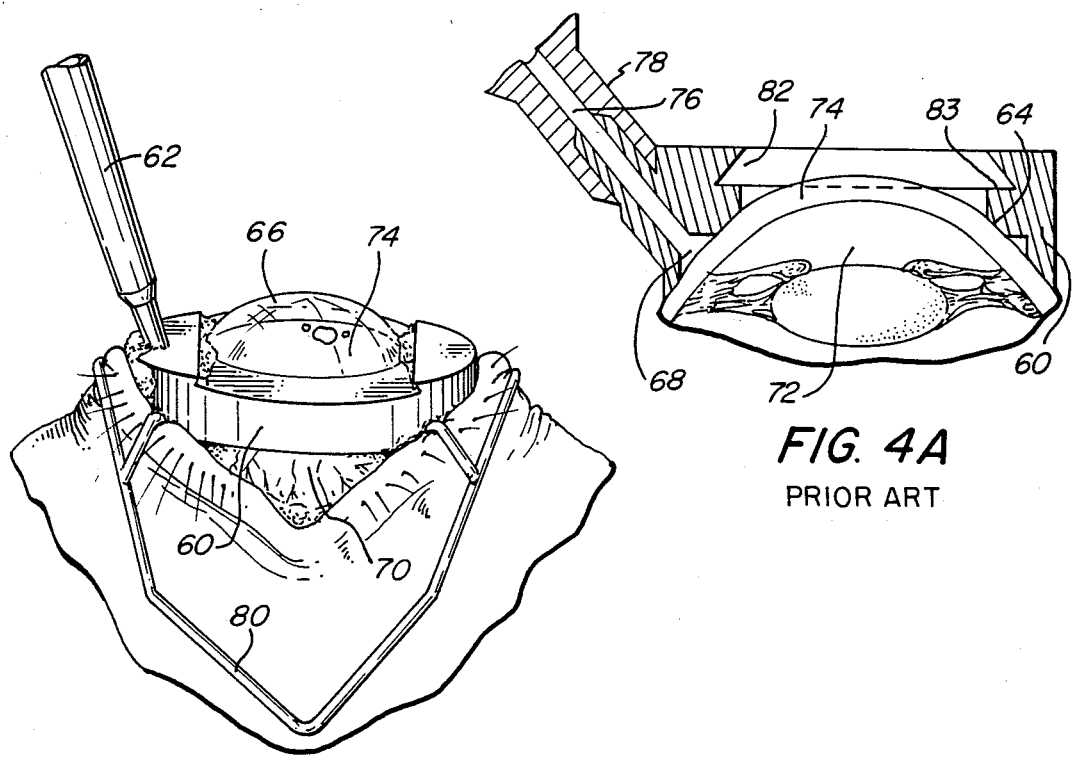
FIG. 4
PRIOR ART
FIG. 4A
PRIOR ART
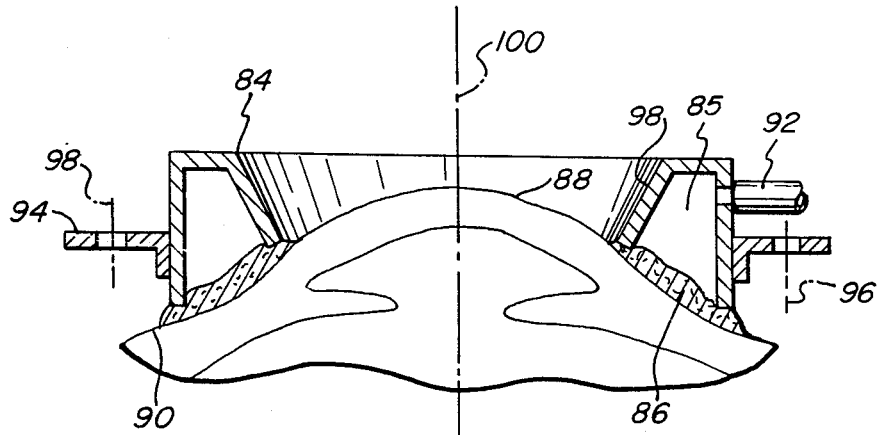
FIG. 5
PRIOR ART

EYE RESTRAINING DEVICE

BACKGROUND OF THE INVENTION

While the invention covers a wide range of applications relating to the fixing and aligning of a patient's head and eye, it is particularly directed to restraining a patient's eye without interfering with the ophthalmic surgery on the exterior surface of the cornea.

When either eye of a patient is undergoing ophthalmic surgery, such as laser refractive keratoplasty (LRK), there is a requirement to control the position and orientation of both the head and eye of the patient. Precise location of a patient's head is particularly critical for LRK where the exterior surface of the cornea of the eye is recontoured or localized defects in the corneal surface are removed or reduced in severity by controlled application of pulsed laser radiation in order to improve the patient's visual capability. The position control can also be of importance during radial keratotomy (RK), linear corneal keratectomy (LCK) or other forms of corneal surgery.

Several different techniques and related apparatus for accomplishing some of these types of surgical procedures are described in publications entitled "Photoablative reprofiling of the cornea using an excimer laser: Photorefractive keratoplasty", by Marshall et al., *Lasers in Ophthalmology*, Vol. 1, No. 1, pp. 21-48 (1986); "Corneal sculpting using an excimer laser delivery system", by Martin et al., *Proc. SPIE*, Vol. 908 (1988); "Beam delivery system for UV laser ablation of the cornea", by Yoder et al., *Proc. SPIE*, Vol. 908 (1988). Also, techniques and apparatus are set forth in U.S. Pat. Nos. 4,665,913; 4,669,466 and 4,718,418 by L'Esperance. Experimental use of ultraviolet lasers in RK has been described by Trokel et al. in an article entitled "Excimer Laser Surgery of the Cornea", *American Journal of Ophthalmology*, Vol. 96, pp. 710-715 (1983). LCK has been described by Seiler et al. in an article entitled "Excimer Laser Keratectomy for Correction of Astigmatism", *American Journal of Ophthalmology*, Vol. 105, pp. 117-124 (1908).

The techniques and apparatus described in the cited references rely on irradiation of the cornea with pulsed laser radiation so that the irradiated tissue ablates with minimal related damage or scarring of adjacent tissue. Implicit in the application of laser radiation of any wavelength to an eye for corrective surgery is the requirement to align the eye and the laser beam accurately so that the ablative effect occurs at the proper location on the corneal surface. Retention of the initially selected alignment throughout the surgical procedure is also a required condition for success.

Prior art devices used to fixate or restrain the head during ophthalmic surgery include a variety of mechanical clamping devices and/or adjustable straps pressing against the patient's forehead, chin, temples and/or cheeks. These devices are generally structurally attached to the hospital gurney, surgical chair or equivalent supporting the patient. However, in some cases the devices are attached to the apparatus used to accomplish the surgical procedure.

Devices previously used to fixate or restrain the eye against voluntary or involuntary motions during surgery include mechanical fixtures with probes penetrating into the scleral tissue, fixtures sutured to the scleral tissue outside the visually-used (corneal) area and vacuum-operated rings contoured to interface with the eye in the general region of the scleracornea juncture (commonly known as the "limbus"). Devices of the latter type have been mentioned in the following articles: *Advanced Techniques in Ophthalmic Microsurgery, Volume two: Corneal Surgery*, by L. J. Girard, C. V. Mosley Company, St. Louis, pp. 156-158 (1981); "Corneal Resurfacing Apparatus and Method", by B. J. Curtin, U.S. Pat. No. 4,173,980, issued Nov. 13, 1979; and "Keratomileusis for Myopia and Aphakia", by J. I. Barraquer, *Ophthalmology*, Vol. 88, p. 701 (1981). Also, similar appliances are described in U.S. Pat. Nos. 4,665,913 and 4,718,418, set forth hereinbefore.

It is a problem underlying the present invention to restrain a patient's head and eye during ophthalmic surgery without interfering with the ability to carry out surgical procedures on the cornea.

It is an advantage of the present invention to provide an eye restraining device and a technique of using same which obviates the limitations and disadvantages of the prior art.

It is still another advantage of the present invention to provide an eye restraining device and a technique for using same to fixate the patient's head and either eye during surgery on an eye.

It is yet another advantage of the present invention to provide an eye restraining device and technique of using same which facilitates positional and angular alignment of the head and eye of a patient with respect to the particular instrument used in performing the surgical procedure.

It is still another specific advantage of the present invention to provide an improved eye restraining device and technique for using same for use in conjunction with surgical techniques and apparatus to reduce excessive myopia, hyperopia and/or astigmatism conditions of the patient's eye.

It is a still further advantage of the present invention to provide an improved eye restraining device and technique for using same to facilitate improvement of the patient's vision through application of LRK surgical procedures involving volumetric removal of corneal tissue with penetration into the stroma to recontour the anterior surface of the cornea or to treat ulcers or other disorders of the cornea.

It is yet a further advantage of the present invention to provide an improved eye restraining device and technique for using same whereby the fixation of the eye does not interfere with optical sighting across the vertex of the cornea and allows water or other fluids administered to the cornea in connection with surgery to drain away from said cornea.

It is another advantage of the present invention to provide an improved eye restraining device and technique for using same which permits surgical removal of the epithelium from the central region of the cornea while the eye is fixated in position and angular orientation.

The invention achieves these objects with apparatus that allows the operator to effectively position and align the eye relative to a laser beam used for LRK procedures although said invention is in no way limited to said procedures, but can be used in many applications wherein a patient's eye is to be fixed in space and oriented for diagnostic or surgical purposes.

Accordingly, there has been provided an eye restraining device including a ring-shaped element which contacts the sclera of an eye so that the cornea projects above the ring-shaped element. A second embodiment includes a head restraint including a plurality of adjustable engaging components for accommodating different sized heads.

BRIEF DESCRIPTION OF THE DRAWINGS

The invention will be illustratively described for preferred and other embodiments in conjunction with the accompanying drawings, in which:

FIG. 4 is a diagram of a prior art eye restraining device;

FIG. 4A is a functional schematic cross-sectional view of the prior art apparatus of FIG. 4;

FIG. 5 is a diagram of another type of prior art eye restraining device;

DETAILED DESCRIPTION OF THE INVENTION

Figure 1:
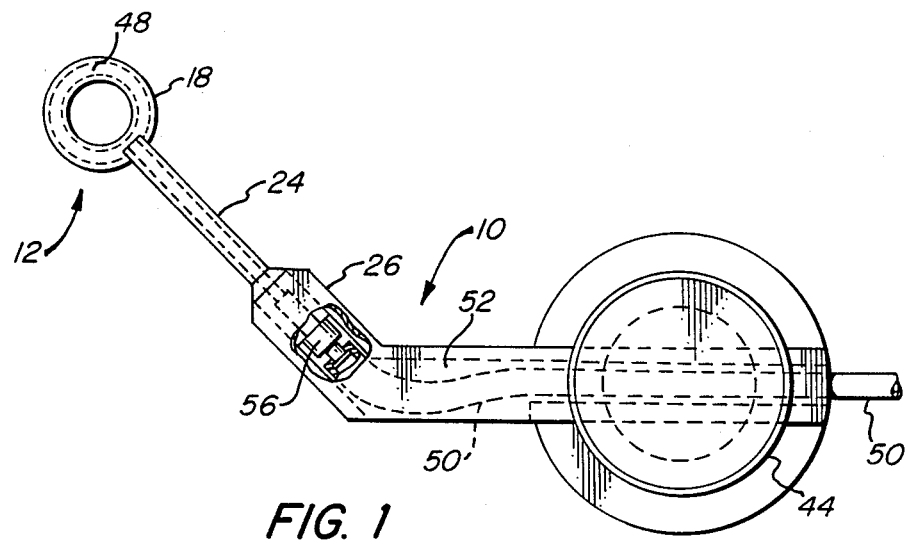
FIG. 1 is a top view of the eye restraining device of the present invention.
Figure 2:
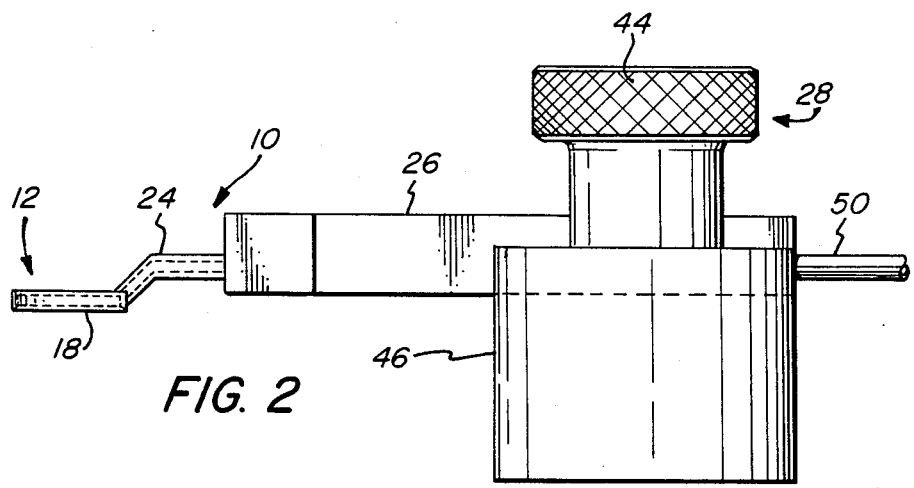
FIG. 2 is a side view, partly in section, of the eye restraining device of FIG. 1.

Referring to FIGS. 1 and 2, there is illustrated an eye restraining device 10 including an element 12 adapted to be secured against the sclera 14 of an eye 16 or positioning and aligning the eye 16. The positioning and aligning structure 12 includes a ring-shaped element 18 adapted to be in contact with the sclera 14 of the eye 16 for enabling the cornea 20 of the eye 16 to project above the ring-shaped element 18.

Reference is directed to FIGS. 1 and 2. These figures depict a preferred embodiment of an eye restraining device 10 that interfaces with a patient's eye 16. Shown are a ring-shaped member 18 supported by an integral angular arm member 24 which is removably connected to a support arm 26. In turn, arm 26 is attached to a cylindrical handle member 28.

Figure 3:
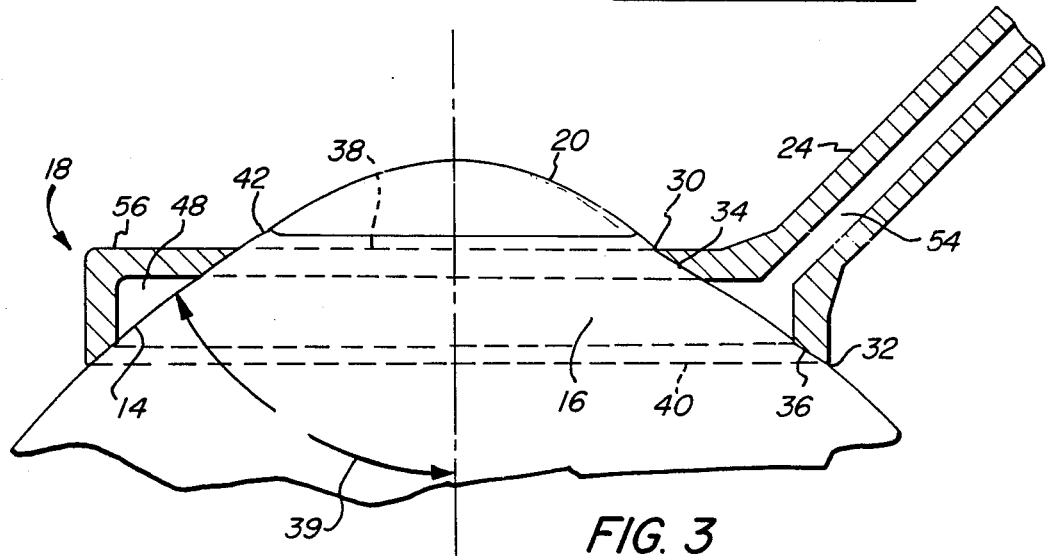
FIG. 3 is an enlarged sectional view of a ring-shaped element interfaced with an eye.

As depicted in the detail view of the ring-shaped member 18 in FIG. 3, member 18 has a triangular annular cross-section. The ring-shaped element 18 has first and second substantially circular apertures 30 and 32, respectively. Each of the apertures includes a seating surface 34 and 36 for engagement with the sclera 14 of eye 16. The first and second substantially circular apertures 30 and 32 have first and second diameters 38 and 40, respectively. The second diameter 40 is larger than the first diameter 38. The first and second surfaces 34 and 36 are aligned with each other and are disposed at an angle 39 of about 46 to about 56 degrees and preferably about 51 degrees for the average use with respect to the centerline of the ring 18 so as to form a favorable interface with the sclera 14 of the eye 16 outside the limbus 42, identified in FIG. 3.

FIG. 3 illustrates the cornea 20 protruding above the ring-shaped member 18 for reasons explained hereinafter. A feature of the present invention is that the outer diameter of the ring-shaped member 18 is minimized so as to fit into the human eye between the upper and lower lids when suitably held apart by a lid speculum of conventional design (see reference numeral 80 in FIG. 4). Since human eyes differ somewhat in size from individual to individual, the ring-shaped member 18 can be constructed in various sizes with a central aperture 30 having a diameter in a range of about 9 to 13 millimeters.

Ring-shaped member 18 and integral arm 24 are preferably constructed from a single piece of plastic material such as polycarbonate. The latter class of materials are easily machined or molded, have relatively low water absorption (typically 0.15% per 24 hour immersion) and are compatible with sterilization.

Most likely, the component comprising elements 18 and 24 would be a single-use item and disposed of following the surgical procedure to obviate sterilization required for repeated use. The supporting arm 26, is preferably made of metal such as stainless steel for strength reasons and to facilitate its mounting interface with handle 28. The latter handle 28 is configured as two parts. The upper portion, having a knurled surface 44 for ease of handling, can be constructed of metal such as aluminum or plastic such as polycarbonate. The bottom portion 46 is preferably constructed of magnetic material such as steel to facilitate attachment to an adjustable mount as discussed hereinafter.

During use, the ring-shaped element 18 is positioned on an anesthetized eye 16 and attached thereto by reducing the air pressure inside the annular cavity 48 with a pressure controller and vacuum pump (not shown) connected to the annular cavity 48 by means of a hose 50 contained within an annular passageway 52 in support arm 26 and an internal passageway 54 through integral arm 24. As indicated in FIG. 1, attachment of hose 50 to the passageway 54 can be accomplished with a metal or plastic fitting 56 threaded or sealed into support arm 26.

In practice, by reducing the pressure within the annular cavity 48 to about 0.02 to 0.2 atmospheres (0.5 to 6 inches of mercury), the ring member 18 is secured by atmospheric pressure firmly but gently against the sclera 14. This pressure effectively secures the eye 16 to the eye restraining device 18. Deformation of the cornea 20 and increase in intraocular pressure are minimized during an ophthalmological operation by keeping the pressure differential small with respect to ambient pressure and by contacting the eye 16 outside the limbus 42. The scleral area exposed to the reduced pressure is intentionally maximized in the design of ring 18 in order that a small pressure differential produces a relatively large ability of the device to oppose motion of the eye during laser surgery. During epithelium removal, the pressure differential may be temporarily increased as long as the intraocular pressure of the eye does not exceed the generally accepted safe level of approximately 65 mm of mercury as measured with a standard tonometer. The small temporary deformation of the sclera which occurs in the localized area encompassed by the partially evacuated cavity is subject to minimal harm or risk of harm.

As noted in FIG. 3, the cornea 20 of the patient's eye 16 projects above the ring-shaped element 18 to facilitate direct optical access from any direction perpendicular to the eye's optical axis in a plane lying just above the top surface 56 of ring 18. This positioning of the ring 18 on eye 16 enables an instrument operator to observe the vertex and thereby facilitate adjustment of the eye's location relative to a laser surgery beam delivery system (not shown). Further, it can be appreciated from FIG. 3 that any fluid, such as water or balanced salt solution, used to irrigate the corneal area 20 in connection with corneal surgery can easily drain from the cornea 20 over the top of the ring 18 for easy disposal. Also, the protrusion of the cornea 20 greatly facilitates access thereto for surgical removal of the epithelium while the eye is restrained with the invention prior to laser surgery.

To contrast the present invention with an example of prior art, attention is directed to FIG. 4 which shows a device for mechanically restraining a patient's eye to preveent voluntary or involuntary rotation in its socket and misalignment of the eye with respect to the incident laser beam during laser surgery. This device, as set forth in the article by Barraquer, described hereinbefore, is essentially a ring 60 with a rigid tubular handle 62 protruding therefrom at a convenient angle. As may be noted in FIG. 4A, the cross section of the ring 60 is functionally similar to that shown in FIG. 3 wherein the open sides 64 and 66 of the hollow annulus 68 interfaces with the sclera surface 70 of the eye 72 outside the cornea 74. A vacuum in the order of 10 inches of mercury is generated within the annular cavity 68 by means of an external vacuum pump (not shown). The air is withdrawn from cavity 68 through air passageway 76 inside the handle 78 and passes to the vacuum pump to cause the ring 60 to adhere to the eye. If the handle (and therefore the ring) is held mechanically or manually fixed with respect to an external instrument or to a laser beam applied to the eye during ophthalmic surgery, alignment of the eye with respect to that instrument or beam will remain more or less constant.

Curtin, in U.S. Pat. No. 4,173,980 described a similar device as part of his "Corneal Resurfacing Apparatus". Eyelid speculum 80 is used with this device to hold the upper and lower eyelids open to accept the ring and to prevent blinking.

A feature of the prior art ring apparatus shown in FIGS. 4 and 4A, that serves no purpose during the laser surgery of interest here, is a dovetail-shaped track 82 intended to allow a microkeratome device to be drawn across the protruding portion of the cornea so as to remove a thin laminar layer of the cornea for replacement or reshaping thereof as part of laminar refractive autokeratoplasty. It should be noted that in order for the apparatus of FIGS. 4 and 4A to allow resection of this laminar layer, the cornea 74 must protrude appropriately above the bottom surface 83 of the track 82. Although not required for the intended use of the prior art device, the track 82 allows limited lateral visual access to the vertex of the cornea 74 from the side. Should use of the device of FIGS. 4 and 4A be attempted in connection with LRK-type surgical procedures, access to the cornea for surgical removal of the epithelium would be found to be very limited.

Another prior art device which can be used to fixate the eye in conjunction with laser surgery, is disclosed by L'Esperance in U.S. Pat. Nos. 4,665,913, 4,669,466 and 4,718,418 and illustrated in FIG. 5. The eye-fixating ring 84 comprises a hollow annulus 85 having an axial-end wall 86 of air-permeable material contoured to engage the exterior surface of the eye on both the cornea 88 and the sclera 90. A side-port connection 92 to an external vacuum pump (not shown) enables the ring 84 to secure itself to the eye by vacuum pressure as generally described hereinbefore. A lug or flange 94 enables rigid, aligned and spaced connection of fixture 84 (and hence the eye) to a supporting structure indicated by the phantom lines 96.

It is apparent from FIG. 5 that this prior art device has the potential for distorting the cornea through influence of the vacuum-constrained contact on surface 90 through wall 86. Further, the recess formed by the intersection of the interior conical wall 98 and cornea 88 can collect fluid such as that used to irrigate the cornea or to humidify its environment in connection with laser surgery. Disposition of this fluid can be a problem. Further, ring 84 projects outward of the vertex of the cornea 88 so visual access to the profile thereof, from a direction perpendicular to the axis 100 of the eye is obscured. This would prevent direct optical sighting across the vertex as desired in setting the location of cornea 88 relative to the laser delivery system (not shown). Further, access to the cornea 88 for the purpose of removing the epithelium prior to corneal surgery while the fixation device is in place would be extremely limited.

Figure 6:
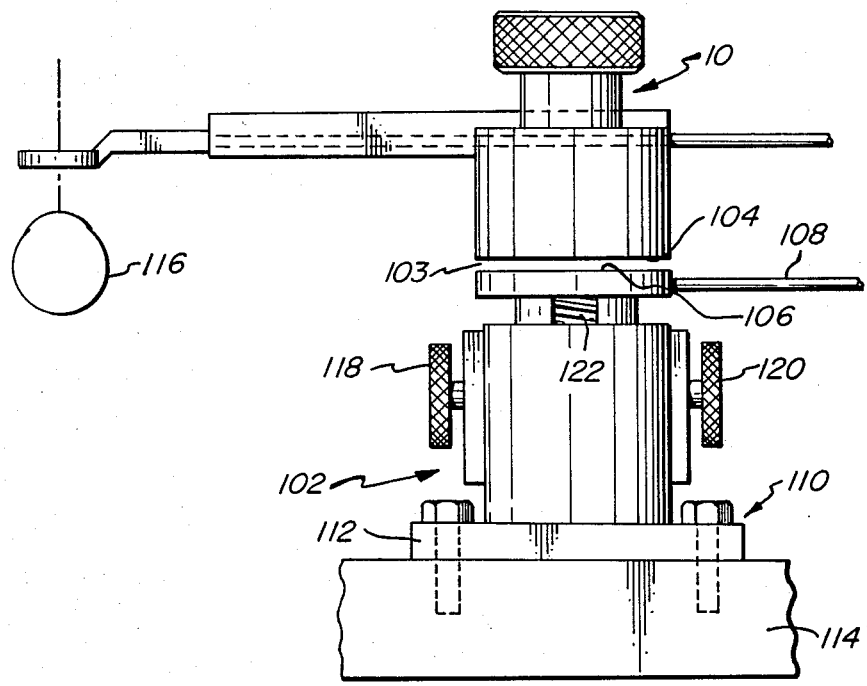
FIG. 6 is a side view of one embodiment of the aforementioned eye restraining apparatus as shown in FIGS. 1 and 2 interfaced with an adjustable support component.
Figure 6A:
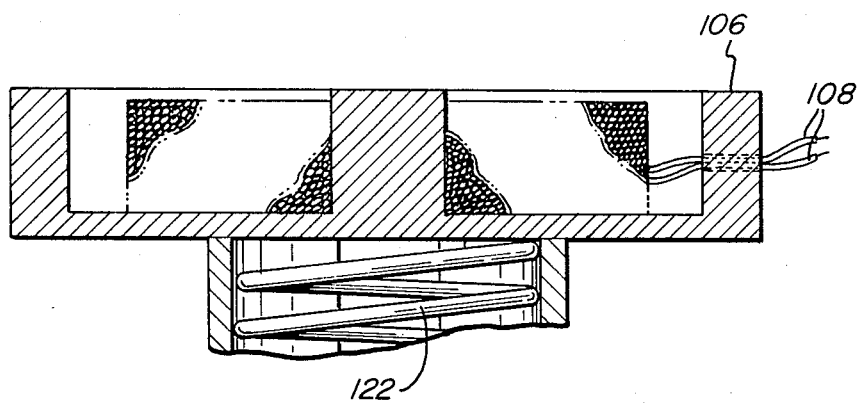
FIG. 6A is a side view, partly in section, of an electromagnet contained within an adjustable support structure.

FIG. 6 shows a side view of the eye fixation device 10 in conjunction with an associated adjustable support structure 102. The interface 103 between components 10 and 102 is comprised of flat surfaces 104 and 106 illustrated as separated for clarity). As mentioned hereinbefore, the interfacing surface 104 on eye fixation apparatus 10 is constructed of steel or other material capable of being magnetized. FIG. 6A illustrates that the corresponding interfacing surface 106 of the adjustable support structure 102 is the pole piece of an electromagnet contained within structure 102 and activated from an external power source (not shown) through cable 108 and controlled by conventional means (not shown), such as a foot switch. Prior to activation of the member 10 can be slid laterally while maintaining contact between surfaces 104 and 106. Misalignment of structure 10 with respect to the center of the polepiece of component 102 can be as large as the radius of the polepiece and can, with typical designs, equal about 2 to 3 centimeters or more without adversely affecting the holding power of the magnetic interface. When the electromagnet is energized, the horizontal location of the eye fixation apparatus 10 is clamped with respect to the adjustable mount 110. The mount 110 is typically attached by any suitable means, such as bolts 112, to structure 114 supporting the patient.

Vertical location of the eye fixation apparatus 10 with respect to the supporting structure 114, and thence with respect to a patient's eye 116, is adjusted by rotating either of the knobs 118 or 120 to activate an internal mechanism such as a rack and pinion 122 to change the elevation of the structure 10 relative to structure 114. Suitable clamping means (not shown), such as a split collar that can be tightened by rotating a clamping knob or ring, can be incorporated into the apparatus. Alternatively, gears used in the height adjusting mechanism can be configured in a helical fashion so as to sufficiently resist axial (vertical) motion so that a separate clamp is not needed.

Figure 7:
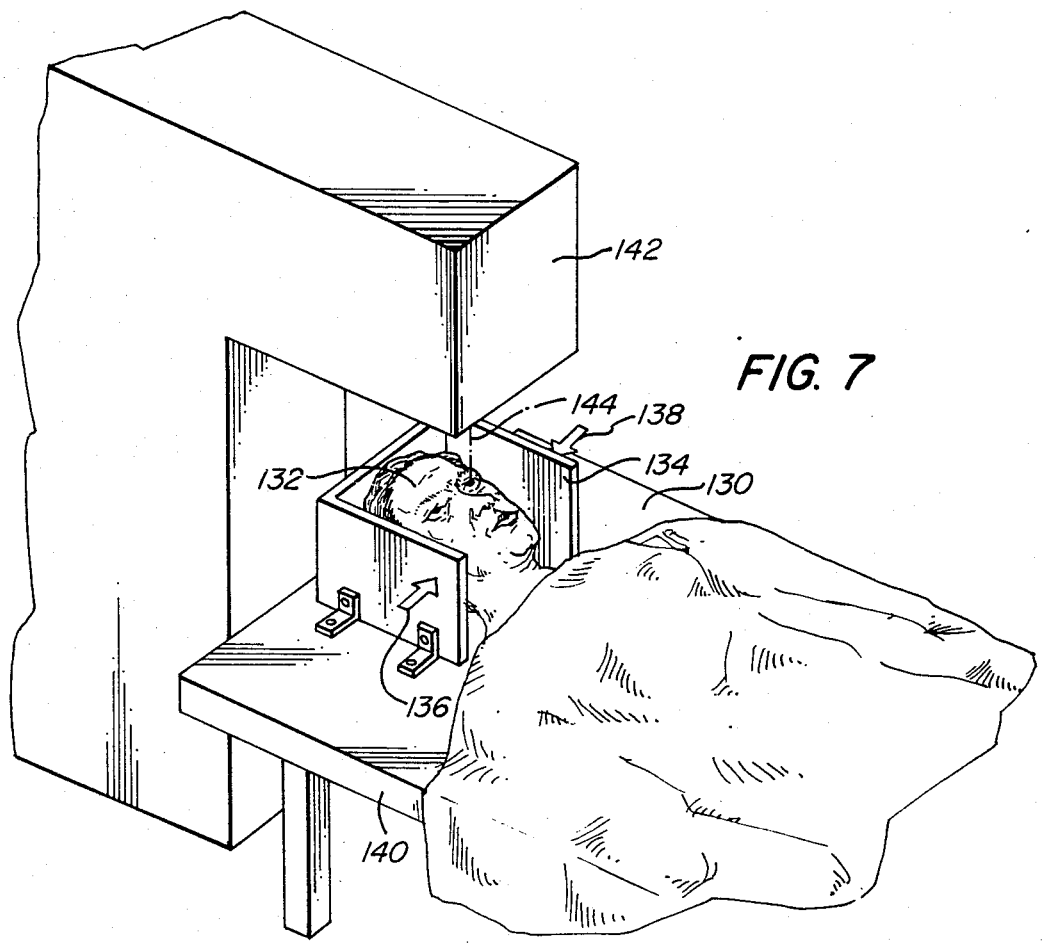
FIG. 7 is a diagram of a prior art head restraint.

FIG. 7 depicts a basic prior art structure 130, disclosed in U.S. Pat. Nos. 4,665,913 and 4,718,418 to L'Esperance for restraining a patient's head 132 during certain types of ophthalmic surgery. A clamp device 134 preferably includes components symbolized at 136 and 138 to stabilize the head through substantially opposed forces exerted at or near the temples. Clamp 134 is secured to the structure 140 (comprising a gurney, surgical chair or equivalent) supporting the patient. Structure 140 is, in turn, positionally adjustable relative to an adjacent apparatus 142 that delivers a laser beam 144 to affect corrective treatment of the patient's eye.

Figure 8:
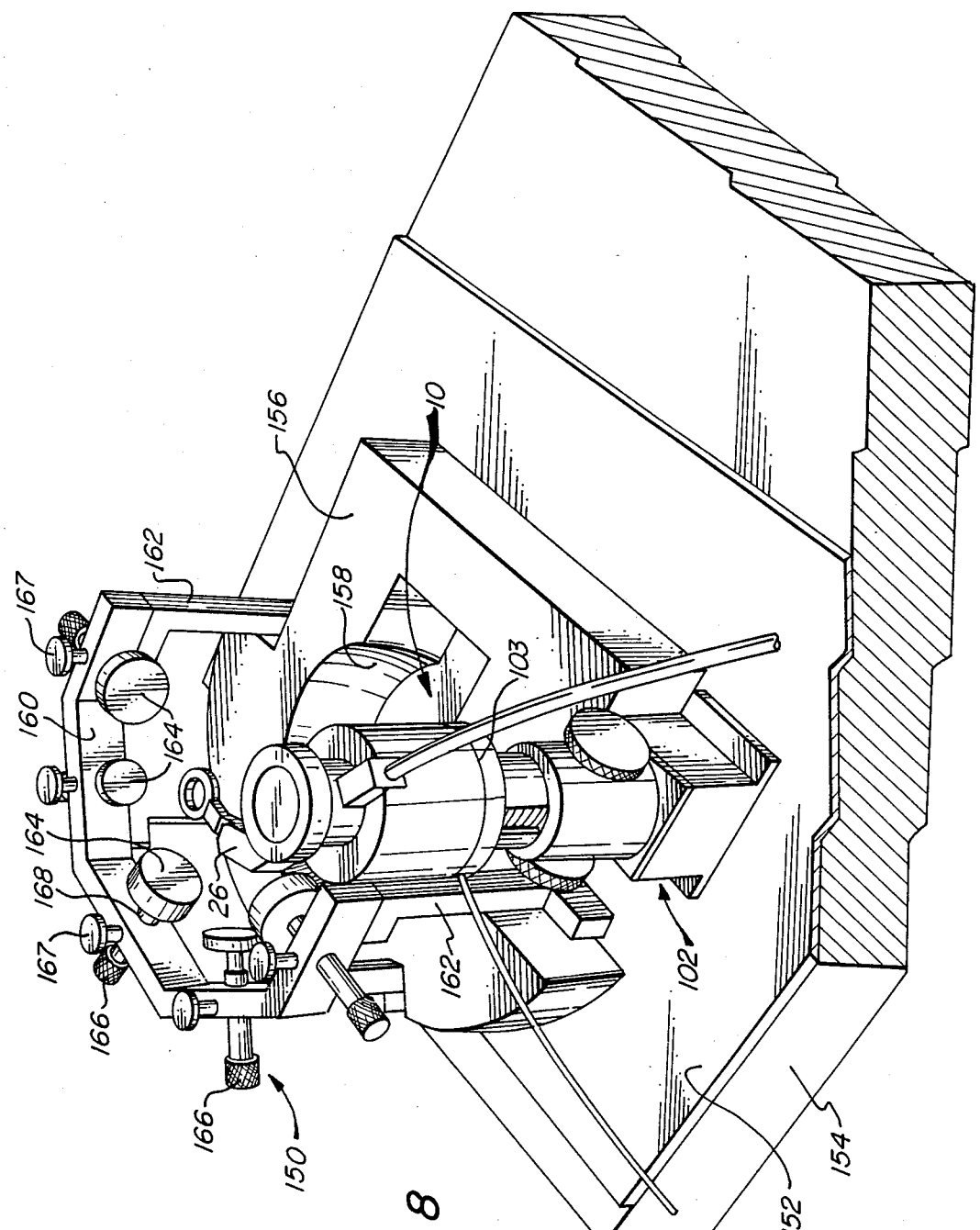
FIG. 8 is an isometric view of one embodiment of the eye restraining device of the present invention combined with the head restraint portion of the present invention.

FIG. 8 depicts an improved form of head restraint apparatus 150 which forms a part of the present invention. It comprises a supporting structure or base plate 152, attached to structure 154 (comprising a gurney, surgical chair or equivalent) which supports the patient's body. The patent's head rests on a pad 156, here shown with an opening 158 to accommodate the back of a patient's head. Pad 156 would typically be made of foam rubber or similar resilient material for patient comfort. A frame 160, supported by three or more legs 162, is attached to plate 152 and partially surrounds the top of the head at approximately the horizontal level of the temples. Three or more pads 164 are arranged at the ends of shafts 166. The shafts 166 can be positioned within holes 168 extending through frame 160 to engage the head at multiple points. The pads 164 are constructed of resilient material, such as foam rubber, for patient comfort and are held in contact with the head through the action of clamp screws 167 secured in place while the pads are manually pressed against the patient's head prior to the operation. The combination of three or more pads 164 then forms a resilient constraint to resist voluntary or involuntary head movement during the surgical procedure. The pads 164 can be covered with easily cleanable and preferably disposable covers (not shown) made of a material such as plastic. The optical axis 170 of the related surgical laser beam delivery system (not shown) is depicted in its approximately nominal position.

FIG. 8 also shows the head restraint 150 in combination with the eye restraining apparatus 10 and the adjustable support 102 of FIG. 6. The apparatus 10 is positioned in relation to the optical axis 170 of the surgical laser beam delivery system (not shown) so that the center of the area to be surgically treated on the patient's cornea is aligned with the laser beam axis. The apparatus configuration of FIG. 8 accommodates surgery on the patient's right eye. If surgery is to be accomplished on the patient's left eye, the adjustable support 102 is moved on plate 152 to the other side of pad 156. The structure 154 is moved laterally by appropriate translation or rotation about a vertical axis so as to allow the left eye to be centered below laser beam axis 170. Alternatively, the adjustable support 102 can be duplicated and mounted to plate 152 so as to accommodate alignment with the patient's left eye. Since the magnetic interface 103 would then be available at either side of the patient's head, interchange between right and left eye in successive patient's would be facilitated. The arm 26 used with the left eye could then be a symmetrically reversed version of that shown in FIG. 1 in order to properly position the ring element 18 with respect to the cornea of the eye.

The patents and articles in this specification are intended to be incorporated in their entireties by reference herein.

It is apparent that there has been provided in accordance with this invention an eye restraining device and a head restraining device which satisfy the objects, means and advantages set forth hereinbefore. While the invention has been described in combination with the embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

What is claimed is:

1. An eye restraining device, comprising:
   means adapted to be secured against the sclera of an eye for positioning and aligning the eye, the means for positioning and aligning the eye including:
      a ring-shaped means for removable attachment to the sclera of the eye;
      handle means attached to said ring-shaped means for positioning said ring-shaped means, said handle means having a first flat surface constructed of a magnetizable material;
   adjustable support means including an electromagnet being selectively clamped to said handle means, said support means having a second flat surface in sliding contact with said first flat surface to facilitate lateral adjustment of said handle means relative to said support means; and
   means for energizing and de-energizing said electromagnet whereby said handle means is selectively clamped to said support means for fixing the position of said ring-shaped means.

2. The eye restraining device of claim 1 wherein said support means further includes means for changing the elevation of said second flat surface to position the ring-shaped means.

3. The process of restraining an eye of a patient, comprising the steps of:
   restraining the head of the patient;
   securing a ring-shaped element against the sclera of the eye;
   positioning the ring-shaped element to align the eye, said step of positioning the ring-shaped element including the steps of:
      providing a handle having a first flat surface connected to said ring-shaped element;
      providing an adjustable support having a second flat surface, said adjustable support including an electromagnet;
      sliding the first flat surface of said handle on the second flat surface of said support to position the ring-shaped element secured to the eye; and
      energizing said electromagnet to clamp said handle to said adjustable support whereby the ring-shaped element fixes the position of the eye.

4. The process of claim 3 further including the step of de-energizing said electromagnet to release said handle from said adjustable support.

* * * * *